United States Patent
Prasad

(10) Patent No.: US 11,192,811 B2
(45) Date of Patent: Dec. 7, 2021

(54) ECONOMICAL PROCESS FOR PREPARATION OF ANAEROBIC GRANULES FOR WASTE WATER TREATMENT

(71) Applicant: Vanita Prasad, Vadodara (IN)

(72) Inventor: Vanita Prasad, Vadodara (IN)

(*) Notice: Subject to any disclaimer, the term of this patent is extended or adjusted under 35 U.S.C. 154(b) by 0 days.

(21) Appl. No.: 16/764,048

(22) PCT Filed: Oct. 31, 2018

(86) PCT No.: PCT/IN2018/050707
§ 371 (c)(1),
(2) Date: May 14, 2020

(87) PCT Pub. No.: WO2019/097538
PCT Pub. Date: May 23, 2019

(65) Prior Publication Data
US 2020/0369545 A1    Nov. 26, 2020

(30) Foreign Application Priority Data
Nov. 14, 2017    (IN) .............................. 201721040610

(51) Int. Cl.
| C02F 3/34 | (2006.01) |
| C02F 3/28 | (2006.01) |
| C02F 1/20 | (2006.01) |
| C12N 1/20 | (2006.01) |
| C02F 101/30 | (2006.01) |

(52) U.S. Cl.
CPC ............. *C02F 3/341* (2013.01); *C02F 3/2846* (2013.01); *C12N 1/20* (2013.01); *C02F 2101/30* (2013.01); *C02F 2305/06* (2013.01)

(58) Field of Classification Search
CPC .... C02F 3/341; C02F 3/2846; C02F 2101/30; C02F 2305/06; C12N 1/20; Y02E 50/30
USPC ....... 210/603, 610, 612, 615, 616, 617, 903, 210/905
See application file for complete search history.

(56) References Cited

U.S. PATENT DOCUMENTS

| 5,723,048 A * | 3/1998 | Kobayashi .............. C02F 11/04 210/603 |
| 7,273,553 B2 * | 9/2007 | Van Loosdrecht ....... C02F 3/12 210/605 |
| 2007/0181493 A1 | 8/2007 | Cote |
| 2015/0336826 A1 | 11/2015 | Peeters |
| 2020/0031698 A1 | 1/2020 | Naider-Fanfan |

FOREIGN PATENT DOCUMENTS

| AU | 2003247036 B2 | 9/2003 |
| IN | 202041032265 | 8/2020 |
| WO | WO 2017/122547 A1 * | 7/2017 |

OTHER PUBLICATIONS

Machine-generated English Translation of WO2017122547, dated Mar. 25, 2021.*

* cited by examiner

*Primary Examiner* — Fred Prince
(74) *Attorney, Agent, or Firm* — Mark M. Friedman

(57) ABSTRACT

The present invention relates to an anaerobic formation of granules for waste water treatment. More particularly, the present invention relates to the use and development of microbial consortia for stimulation of anaerobic digestion of organic matter and to a method for enhancing the granulation rate of suspended anaerobic sludge using carbohydrate rich industrial effluent.

10 Claims, 5 Drawing Sheets

ECONOMICAL PROCESS FOR PREPARATION OF ANAEROBIC GRANULES FOR WASTE WATER TREATMENT

FIELD OF THE INVENTION

The present invention relates to the economical way of production of the biomass of anaerobic granules for start-up/restart of UASB reactors used for the treatment of waste water. More particularly, the present invention relates to the use and process for preparation of microbial consortia for stimulation of anaerobic digestion of organic matter and to a method for enhancing the granulation rate of suspended anaerobic sludge using carbohydrate rich industrial effluent.

BACKGROUND OF THE INVENTION

Waste waters from industrial processes or from municipal sewage contain significant amounts of organic matter that must be removed. Of various treatment methods available, Anaerobic Digestion (AD) is one of the key technology for waste treatment at economical cost.

Many studies in the field of anaerobic wastewater treatment have resulted in significant indications about the role importance of sludge granules in biodegradation waste using anaerobic process. The development of anaerobic granules is principally attributed to the formation of anaerobic granules in sludge bed, where by the microbial communities are playing very important role of digesting the substrates to produce biogas.

A sludge granule is an aggregate of microorganisms that is often formed during wastewater treatment in the absence of any support matrix such as, for example in a constant up flow hydraulic regime. Under these conditions, the microorganisms present survive and proliferate by attaching to each other.

The aggregates of microorganisms eventually form dense granules, typically with a diameter in the range of from 0.5 to 5 mm, often referred to as granular sludge. Due to their high density and therewith high settling rates, granular sludge resists washing out from a wastewater treatment reactor, even at high hydraulic loads.

Since granular sludge has a high density, it has a high settling velocity. One gram of granular sludge is typically able to convert in the range of from 0.1 to 1.0 grams of Chemical Oxygen Demand (COD) per day into methane.

An optimal treatment method is to make use of high rate anaerobic digester like UASB, EGSB and IC reactors. Third generation anaerobic digesters have a noticeable biomass retention capacity, resulting in a much higher solids retention time (SRT) than a hydraulic retention time (HRT). Immobilization of biomass without a support material was first observed in UASB reactors as a result of granule formation (Lettinga et al. 1980).

In these reactors granulated biomass is retained by virtue of the good settleability of such biomass and the design of special separators internal to the reactors that can effectively separate and retain such granular biomass often referred to as granular sludge.

Understanding granule structure and development are key issues for controlling its formation. MacLeod et al. (1990) proposed a three-layer structure model for granules developed in UASB reactors: an exterior layer with heterogeneous population, a middle layer containing H2-producing and H2-consuming micro-organisms, and a core dominated by acetotrophic methanogens. Bacterial composition and the structure of granular methanogenic sludge depend upon the type of substrate used.

As this is governed solely by microbial activity, its proper development and optimization is very important. The granulation and enhancement of the essential microbial community is a complex science and it is very hard to produce in field condition.

Therefore, in this study a cost-effective process has been developed and optimized using the fundamental process of granulation in UASB reactor. The growth process of the particles required stabilizing operation, avoiding the particles washouts, which are mostly assessed to be as the main concern of granules growing.

In anaerobic digesters the growth of new grown biomass is low (<4% of COD is used for growth), due to this the total quantity produced in the system is low and constant wash out is another issue.

Moreover, for start-up of new systems huge quantity of granular biomass is required. Seeding of new digester systems with such granular biomass reduces the start-up time from several months, or even up to a year, to few weeks only.

Further to restart high rate anaerobic reactor after shock load, there is a need anaerobic granular biomass. But prior methods to produce granulated sludge requires addition and mixing of chemicals (polymeric and inert) in different tank. Hence increasing the cost of production of active granules on large scale.

A liability of the anaerobic process in previous systems has been in loss of biomass in the anaerobic reactors, particularly those that are structured to use granulated biomass. A particularly well suited anaerobic reactor is known as an Upflow Anaerobic Sludge Blanket reactor (UASB), which utilizes fluidized biomass granules in an upflowing configuration.

Prior USAB reactors have shown a tendency to lose biomass granule inventory over time, as the effluent from the anaerobic reactor flows into the aerobic reactor. The lost biomass granule must be replaced with an outside source of granules which adds cost to the process and risks upset to the system. Furthermore, another problem in the existing anaerobic reactors is that they tend to have a significant build-up of heavy metals over time.

The present invention relates to the increase in efficiency of biomass granulation rate of suspended anaerobic sludge in a cost effective manner by exploiting inherent properties of bacteria to form granules and using carbohydrate rich effluent.

In this method no external additive has been used. So it makes the development process economical which is essential to decrease the cost of granular biomass production as it considered very important product for successful commissioning and smooth operations of advanced, energy efficient anaerobic waste/wastewater treatment plants.

In India many STP and ETP are based on this anaerobic technology but there full potential is not exploited yet due to the issue of availability of Granulated biomass sludge.

The present invention overcomes the above many problems associated with start-up and operation of high rate anaerobic reactors used in Wastewater treatment systems. The invention reduces or eliminates the need for costly import of granulate sludge, disposal of activated sludge and provides an economized solution for treatment of wastewater.

SUMMARY OF THE INVENTION

The present relates to the economical way of production of the biomass of anaerobic granules for start-up/restart of UASB reactors used for the treatment of waste water.

According to one aspect of present invention was the seed sludge selection. The sludge which was highly fluffy in nature, pH variation of less than 0.1 pH units after being separated from the digester and has VSS content of 15000 mg/l and specific methanogen activity of 0.28 l/gm VSS and but was not having granules above 1 mm.

According to another aspect of the invention is the development of selected seed sludge toward granulation by feeding selected seed sludge with specific sterile growth medium (Various low to high strength glucose media) in scotch bottle of 250 ml capacity and incubating it in incubator-shaker to cultivate biomass in a batch system for faster granulation.

Increase in number of Granules was between 108% and 592% was observed over the 9 to 24 day incubation period.

According to another aspect of the invention is the mass cultivation of selected biomass at ambient temperature and neutral pH. Many kinds of microorganisms are acclimatized in mesophilic temperature range therefore the optimum range between (22-40° C.) for microorganisms growth is achieved and an organic loading rate of 2.5-16.2 kg COD/m3·d has been used. In general, the environment was neutral pH and typical values of alkalinity be in range of 750-1500 mg/l.

According to another aspect of the invention is the design optimization of reactor vessel to prepare anaerobic granules. The laboratory-scale UASB reactor is made from glass cylinders with inside diameter 0.105 m and height of 1 m, giving a total effective reactor volume of 8.6 L. At the top of the reactor is the gas/liquid/solid separator. Gas collection has been done by means of a hollow inverted cone. Clarified effluent flowed over to the collection vessel, while solids which settle out, were returned into the reactor by gravity. The height and design of gas liquid separator is modified to reduce the TSS content of the effluent. The reactor inlet from bottom was kept flat with many evenly spaced inlet feed ports discharging feed in a horizontal as well as vertical direction. Sampling ports were evenly spaced along the length of the reactor.

According to another aspect of the invention is to prepare biomass granules within 90-120 days from selected seed prepared using media containing Pure carbohydrate. In UASB reactors granule growth can be enhanced artificially if a certain set of environmental conditions are met. These conditions included a pH between 4.0 and 9.0, simple sugars in the feed medium and a source of nitrogen, phosphate and Trace elements (vitamins and minerals essential for microbial growth).

According to another aspect of the invention is to grow granulated biomass using carbohydrate rich industrial effluent especially from food processing industry effluents. These effluents used as substrate consists of sugars with negligible nitrogen content and with adequate nutrients and trace elements for growth were able to produce granular biomass at very fast pace and doesn't need any external additive material like polymers etc.

According to another aspect of the invention, the growth yield of the granules of biomass in the anaerobic zone is more than 10 times greater for about 60-80% of the seed biomass.

According to another aspect of the invention is the method for the treatment of carbohydrate rich wastewater in an anaerobic reactor for production of granules of the biomass by supplementing with growth stimulating solutions. It was surprising to observe that some specific multivalent cations (B, Fe, Mn, Mg, Zn, Co, Ni, Al, Na, K Ca, Cu, Mo, Se, W etc.) and Vitamins (folic acid, biotin, nicotinic acid and Vitamin B1, B2, B6, B12 etc.) added as growth enhancing solution helped in the successful granules formation/granulation process.

According to another aspect of the invention is the method for the treatment of sewage and industrial effluents which includes significant reduction of COD and BOD from the wastewater. It was observed that granular biomass produced higher biogas yield along >90% COD and BOD reduction in waste water.

According to another aspect of the invention is the method to the use of only microorganisms for stimulation of anaerobic digestion of organic matter and a method for enhancing the granulation rate of suspended anaerobic sludge wherein 99% of granulation of biomass is done.

According to another aspect of the invention is the study of diversity of Bacterial communities using metagenomics and surprisingly we found that 18-25% of the bacterial population are Archaea of which 45-48% is mixed function, 32-35% is hydrogenotrophic and rest are acetogenic.

According to another aspect of the invention is to store granular biomass and perform its stability study. It was observed that there is no deterioration in biomass methanogenic activity and was functioning at 100% efficiency when reused after 6 months of storage time.

According to another aspect of the invention is the availability of ready to use granulated biomass to reduce start-up time of high rate reactors to weeks rather than months or years. Moreover, will help operators to recover reactors after a shock load.

According to another aspect of the invention is production of liquid fertilizer as the treated water is rich in nitrogen (TKN 7-9 mg/l), phosphorus (10-50 mg/l), potassium (3-9 mg/l) and calcium (150-350 mg/l) hence can be directly used for irrigation of farm land.

One of the aspect of the invention is invention is a process for preparation of anaerobic granules for waste water treatment wherein the anaerobic consortia is microorganism selected from the group consisting of a microorganism strain S3/H4 MCC Accession No. 0116, so as to thereby degrade the material in the sludge.

The foregoing aspects of the invention are illustrative of those that can be achieved by the present invention and are not intended to be exhaustive or limiting of the possible advantages which can be realized. Thus, these and other aspects of the invention will be apparent from the description herein or can be learned from practicing the invention, both as embodied herein or as modified in view of any variation which may be apparent to those skilled in the art.

DESCRIPTION OF THE INVENTION

Figure 1:
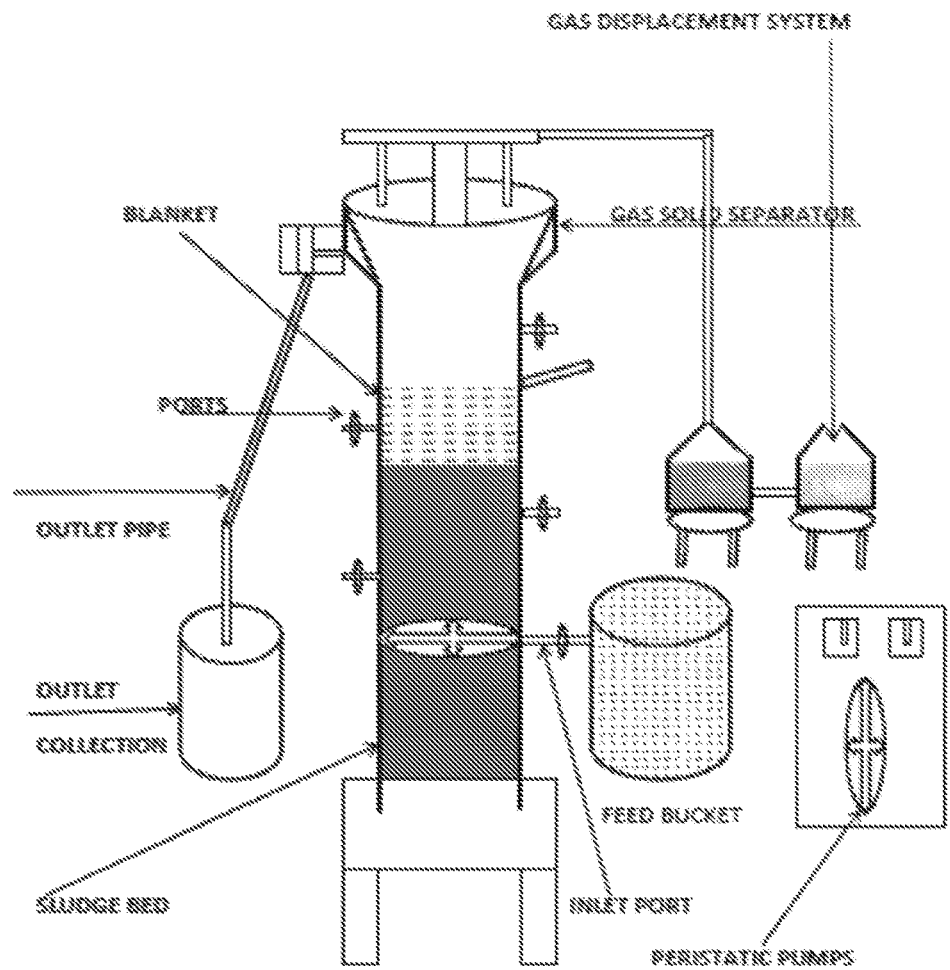
FIG. 1 illustrates UASB Lay out
Figure 2:
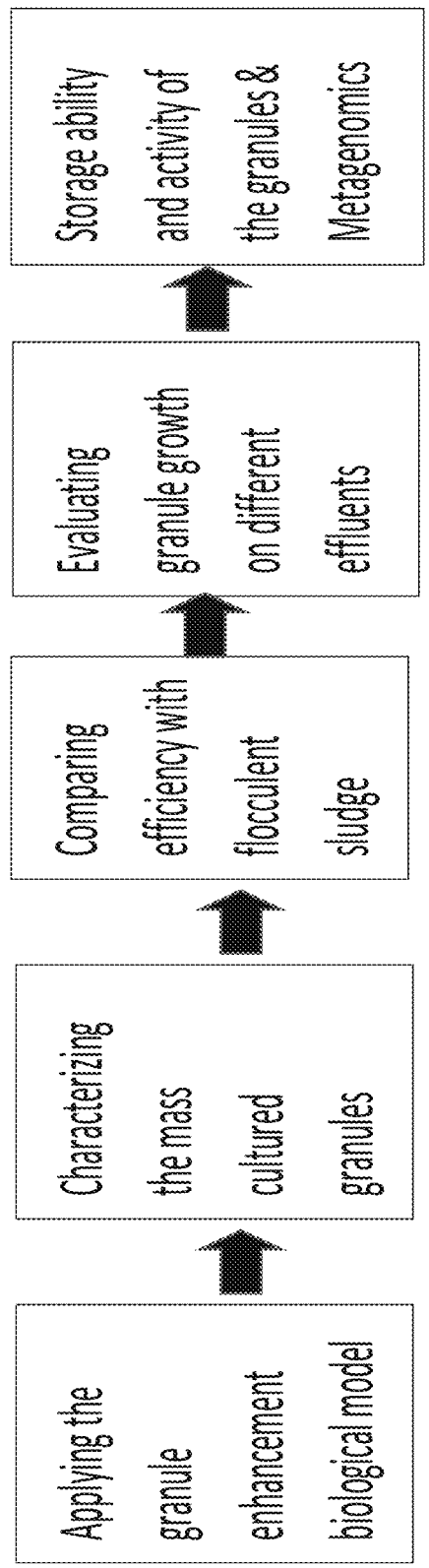
FIG. 2 illustrates block diagram of Process Flow

The present invention relates to the economical way of production of the biomass of anaerobic granules for start-up/restart of UASB reactors used for the treatment of waste water.

One of the embodiment of present invention is to reduce or eliminate the need for costly import of granulate sludge, disposal of activated sludge and provides an economized solution for treatment of wastewater.

Another embodiment of the present invention was the seed sludge selection. The sludge which was highly fluffy in nature, pH variation of less than 0.1 pH units after being separated from the digester and has VSS content of 15000 mg/l and specific methanogen activity of 0.28 l/gm VSS and but was not having granules above 1 mm. The term VSS herein refers to Volatile suspended solids (VSS) is a water quality measure obtained from the loss on ignition of the mass of measured total suspended solids.

One of the embodiment of the invention is the development of selected seed sludge toward granulation by feeding selected seed sludge with specific sterile growth medium (Various low to high strength glucose media) in scotch bottle of 250 ml capacity and incubating it in incubator-shaker to cultivate biomass in a batch system for faster granulation. Increase in number of Granules was between 108% and 592% was observed over the 9 to 24 day incubation period.

One of the embodiment of the invention is the mass cultivation of selected biomass at ambient temperature and neutral pH. Many kinds of microorganisms are acclimatized in mesophilic temperature range therefore the optimum range between (22-40)° C. for microorganisms growth is achieved and an organic loading rate of 2.5-16.2 kg COD/m3·d has been used. In general, the environment was neutral pH and typical values of alkalinity be in range of 750-1500 mg/l.

One of the embodiment of the invention is the design optimization of reactor vessel to prepare anaerobic granules. The laboratory-scale UASB reactor is made from glass cylinders with inside diameter 0.105 m and height of 1 m, giving a total effective reactor volume of 8.6 L. At the top of the reactor is the gas/liquid/solid separator. Gas collection has been done by means of a hollow inverted cone. Clarified effluent flowed over to the collection vessel, while solids which settle out, were returned into the reactor by gravity. The height and design of gas liquid separator is modified to reduce the TSS content of the effluent. The reactor inlet from bottom was kept flat with many evenly spaced inlet feed ports discharging feed in a horizontal as well as vertical direction. Sampling ports were evenly spaced along the length of the reactor.

The anaerobic reactor plays a role of performing anaerobic treatment to wastewater to generate biogas such as methane gas and treat contaminants in the wastewater or organic materials. In detail, the anaerobic reactor is configured to have a cylindrical shape and operates in an anaerobic state, wherein no support material or polymer is used with agglutination of bacterial anaerobes. Wastewater/organic materials is introduced from the bottom portion of the anaerobic reactor, flows upwards and is discharged through the upper portion of the anaerobic reactor. In the reactor wastewater/media/pure organic carbohydrate effluent is introduced to the anaerobic reactor, organics are removed by means of anaerobic treatment and granules produced and simultaneously biogas such as methane gas is produced.

One of the embodiment of the invention is to prepare biomass granules within 90-120 days from selected seed prepared using media containing Pure carbohydrate. In UASB reactors granule growth can be enhanced artificially if a certain set of environmental conditions are met. These conditions included a pH between 4.0 and 9.0, simple sugars in the feed medium and a source of nitrogen, phosphate and Trace elements (vitamins and minerals essential for microbial growth).

One of the embodiment of the invention is to grow granulated biomass using carbohydrate rich industrial effluent especially from food processing industry effluents. These effluents used as substrate consists of sugars with negligible nitrogen content and with adequate nutrients and trace elements for growth were able to produce granular biomass at very fast pace and doesn't need any external additive material like polymers etc.

One of the embodiment of the invention, the growth yield of the granules of biomass in the anaerobic zone is more than 10 times greater for about 60-80% of the seed biomass.

Another embodiment of the invention is the method for the treatment of carbohydrate rich wastewater in an anaerobic reactor for production of granules of the biomass by supplementing with growth stimulating solutions. It was observed that some specific multivalent cations (B, Fe, Mn, Mg, Zn, Co, Ni, Al, Na, K Ca, Cu, Mo, Se, W etc.) and Vitamins (folic acid, biotin, nicotinic acid and Vitamin B1, B2, B6, B12 etc.) added as growth enhancing solution helped in the successful granules formation/granulation process.

One of the embodiment of the invention is the method for the treatment of sewage and industrial effluents which includes significant reduction of COD and BOD from the wastewater. It was observed that granular biomass produced higher biogas yield along >90% COD and BOD reduction in waste water.

One of the embodiment of the invention is the method to the use of only microorganisms for stimulation of anaerobic digestion of organic matter and a method for enhancing the granulation rate of suspended anaerobic sludge wherein 99% of granulation of biomass is done.

One of the embodiment of the invention is the study of diversity of Bacterial communities using metagenomics and surprisingly we found that 18-25% of the bacterial population are Archaea of which 45-48% is mixed function, 32-35% is hydrogenotrophic and rest are acetogenic.

One of the embodiment of the invention is to store granular biomass and perform its stability study. It was observed that there is no deterioration in biomass methanogenic activity and was functioning at 100% efficiency when reused after 6 months of storage time.

One of the embodiment of the invention is the availability of ready to use granulated biomass to reduce start-up time of high rate reactors to weeks rather than months or years. Moreover, will help operators to recover reactors after a shock load.

One of the embodiment of the invention is production of liquid fertilizer as the treated water is rich in nitrogen (TKN 7-9 mg/l), phosphorus (10-50 mg/l), potassium (3-9 mg/l) and calcium (150-350 mg/l) hence can be directly used for irrigation of farm land.

The present relates to the economical way of production of the biomass of anaerobic granules for start-up/restart of UASB reactors used for the treatment of waste water.

One of the embodiment of the invention is to reduce or eliminate the need for costly import of granulate sludge, disposal of activated sludge and provides an economized solution for treatment of wastewater.

One of the embodiment of the invention is a process for preparation of anaerobic granules for waste water treatment wherein the anaerobic consortia is microorganism selected from the group consisting of a microorganism strain S3/H4 MCC Accession No. 0116, so as to thereby degrade the material in the sludge. The term consortia used herein is a microbial consortium of two or more microbial groups living symbiotically. Consortiums can be endosymbiotic or ectosymbiotic.

For granulation of sludge we have used "sludge" means sludge from municipal sewage disposal plants, manure treatment systems, excess aeration or anaerobic sludge from industrial ETPs (such as dairy, food industry, paper and pulp etc). Any sludge being useful as a source as seed for the process of granule formation in an anaerobic condition may be used according to the seed selection method used in the present invention.

Example 1: Seed Sludge Development Toward Granulation

Seed sludge and feed selection experiments has been done in scotch bottle of 250 ml and Incubator-shaker has been used to cultivate biomass in a batch system at ambient temp and neutral pH has been maintained. The batch systems consisted of units containing 250 ml of each specific sterile growth medium (Various low high strength glucose media) inoculated with 100 ml sludge. Sludge brought from sewage plant was highly fluffy in nature, pH variation of less than 0.1 pH units has been observed after being separated from the digester and it has VSS content of 15000 mg/l and specific methanogen activity of 0.28 l/gm VSS which 60-61% of MLSS and having bacterial aggregates of size below 1 mm.

Feed Selection:

Granules are described as spherical bio-film consisting of a densely packed symbiotic microbial consortium, living in a symbiotic environment in absence of any support matrix. Therefore, if this granulation process can be aided by any means, it would aid immensely in the applicability of arguably the most cost-effective means of removing organic waste from effluent streams namely high rate anaerobic digestion (or the UASB/EGSB systems to be more exact). As per art, in most biological systems, the inorganic species nitrogen, phosphates and calcium (except for carbon, oxygen and hydrogen) play an important role in granule growth. Phosphate, calcium and simple sugars are also vital for the granulation process to occur, as they are used in extra cellular polysaccharide production and the initial cell attachment process (nucleus formation).

Figure 3:
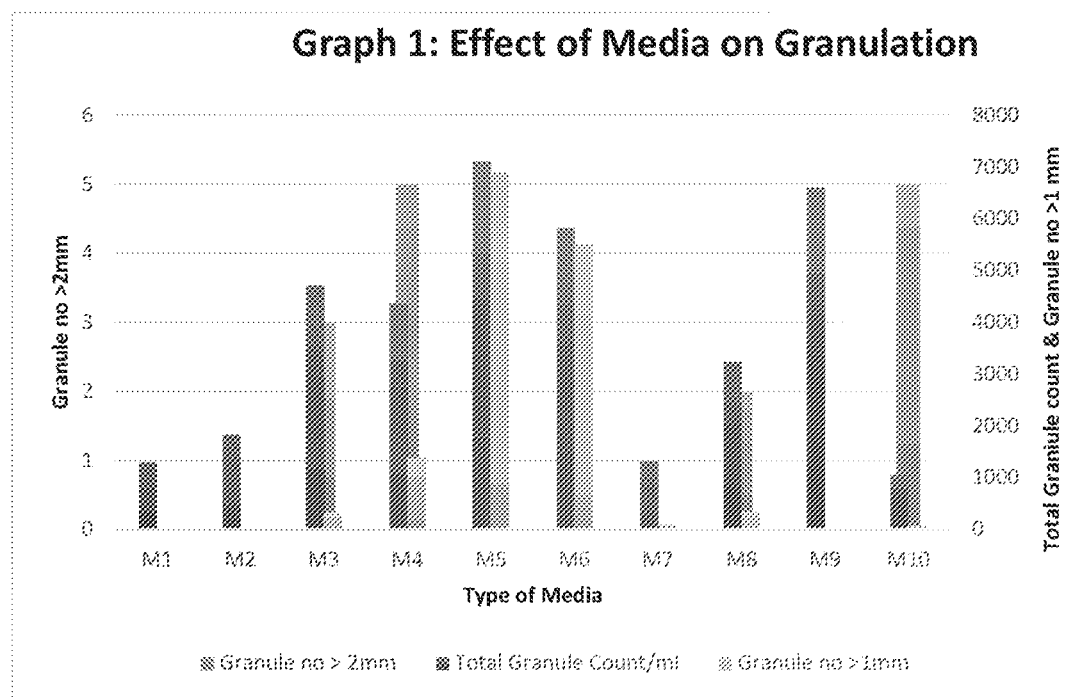
FIG. 3 illustrates Graph 1 of Effect of Media on Granulation
Figure 4:
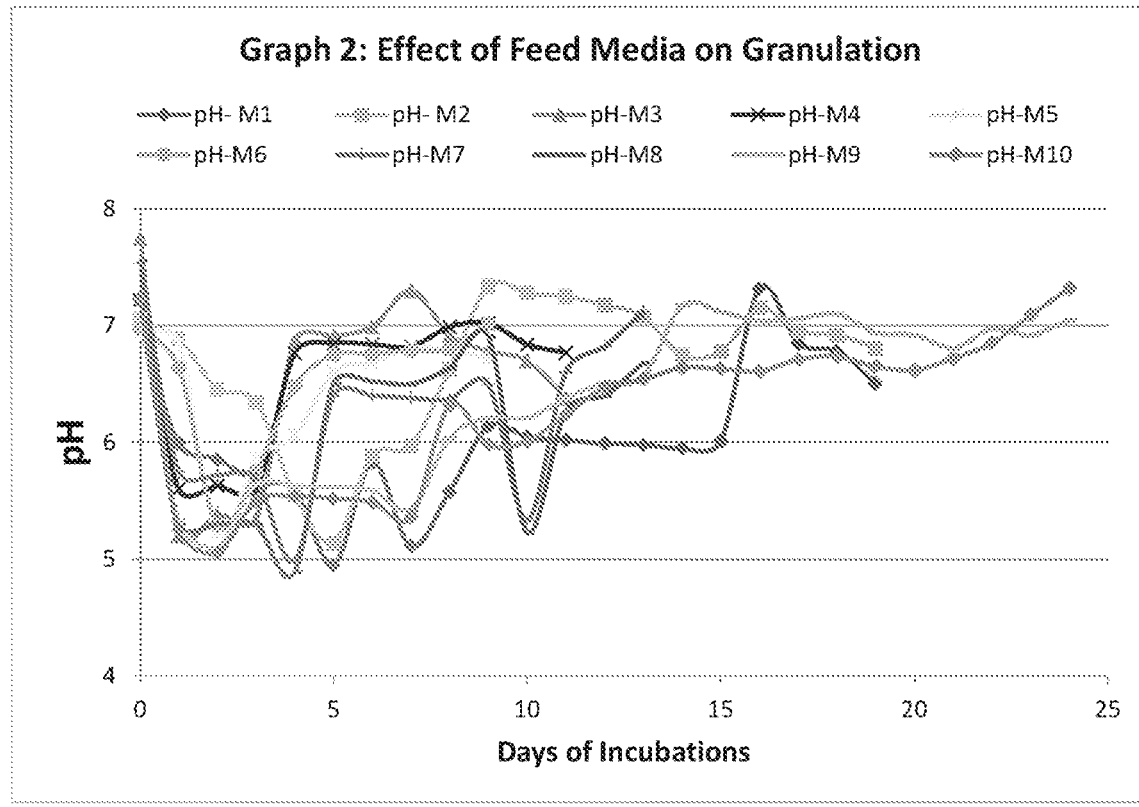
FIG. 4 illustrates Graph 2 of Effect of Feed Media on Granulation

Studies done earlier showed that granulation can be artificially enhanced on lab-scale. Therefore, we have also initiated our experiment for feed selection in scotch bottle of 250 ml. n Incubator-shaker has been used to cultivate biomass in a batch system at 40° C. and 80 r·min-1. The batch systems consisted of units containing 250 ml of each specific sterile growth medium inoculated with 100 ml sludge from a Sewage treatment plant. Various media are used and their effect on pH and granulation is shown in Graph 1 and 2 of FIGS. 3 and 4 respectively Increase in number of Granules had been observed 108% to 592% over the 9 to 24 day incubation period, depending on the media used (Graph I). The formation of very small granules (sizes varying from 1 to 2 mm) were found by 3rd day with the high strength glucose media indicated by dark colour of the solution. In addition, it is observed that in comparison to the original sludge inoculum, a clear fast-separating granular sludge layer has been evident at the end of the incubation period. For the high strength glucose media, maximum increase in granule number of 592% was found.

Example 2: Procedure for Production of Anaerobic Granulated Biomass for Waste Water Treatment/Organic Matter Degradation The laboratory-scale UASB reactor (FIG. 1) has been made from glass cylinders with inside diameter 0.105 m and height of 1 m, giving a total effective reactor volume of 8.6 l. At the top of the reactor is the gas/liquid/solid separator. Gas collection has been achieved by means of a hollow inverted cone. Clarified effluent flowed over to the collection vessel, while solids which settle out, are returned into the reactor by gravity. Temperature in the reactor has been maintained at ambient temperature (20-40 C). The reactor plays a role of performing anaerobic treatment to wastewater to generate biogas such as methane gas and treat contaminants in the wastewater or organic materials. In detail, the anaerobic reactor is configured to have a cylindrical shape and operates in an anaerobic state, wherein no support material or Polymer is used with agglutination of bacterial anaerobes. Wastewater/organic materials is introduced from the bottom portion of the anaerobic reactor, flows upwards and is discharged through the upper portion of the anaerobic reactor. In the wastewater/media/pure organic carbohydrate effluent is introduced to the anaerobic reactor, organics are removed by means of anaerobic treatment and granules produced and simultaneously biogas such as methane gas is produced.

Example 3: Granules Preparation

Seed prepared in Lab has been used to start the UASB reactor. Media containing pure carbohydrate and carbohydrate rich industrial effluent has been applied to the biomass with continuous feeding for 120 days Table 1. Development of granules was first done using synthetic media containing pure carbohydrate in Lab scale UASB reactor as outlined in FIG. 1. The same sludge granulation development has been done at similar loading rates using various food processing industry effluents. These substrates mainly consists of sugars with negligible nitrogen content and with adequate addition of nutrients & trace elements for growth.

TABLE 1

Variation in Granule size during Incubation Period

| Incubation Time | Granule Count/ml | Granule size > 1 mm | Granule size > 2 mm | MLSS (mg/l) | MLVSS (mg/l) i.e. VSS content |
|---|---|---|---|---|---|
| Initial - 0 Day | 1100 | 100 | 0 | 12030 | 5995 |
| After- 60 Days | 6240 | 5500 | 200 | 26040 | 13670 |
| Final - 120 Days | 30132 | 17280 | 5832 | 89480 | 56372 |

It is to be noted that many kinds of microorganisms are more acclimatized in mesophilic temperature range therefore the optimum range between (20-40° C.) for microorganisms growth was used and an organic loading rate of 2.5-16.2 kg COD/m3·d has been used as represented in Table 2. In general, neutral pH typical values of alkalinity 750-1500 mg/l some specific multivalent cations (multivalent cations (B, Fe, Mn, Mg, Zn, Co, Ni, Al, Na, K Ca, Cu, Mo, Se, W etc.) and Vitamins (folic acid, biotin, nicotinic acid and Vitamin B1, B2, B6, B12.) for the successful granules formation/granulation process.

The following parameters were monitored for granule development: pH, Total Solids (TS); Mixed Liquor Suspended Solids (MLSS), Mixed Liquor Volatile Suspended Solids (MLVSS), Ash Content, Volatile Fatty Acids (VFA's) and Alkalinity has been determined using Standard Methods of APHA.

TABLE 2

Granule Size & Efficiency Optimization

| Days | Size of Granules (~mm) No/10 ml at 1:10 dilution | Loading Rate (g COD/L/day) | Gas Produced (L/day) | COD Reduction (%) | BOD Reduction (%) | VFA/ALK Ratio | TSS (mg/L) | VSS (mg/L) |
|---|---|---|---|---|---|---|---|---|
| 0-30 | <1 (1000)<br>>1 (100)<br>2 (nil) | 2.5 | 1.4 | 55 | 70 | 0.6 | 512 | 287 |
| 30-60 | <1 (540)<br>>1 (5500)<br>>2 (200) | 16.2<br>6<br>10.4 | 1.3<br>2.6<br>4.1 | 68<br>87<br>87 | 52<br>77<br>80 | 0.6<br>0.21<br>0.13 | 490<br>184<br>48 | 343<br>142<br>42 |
| 60-120 | <1 (17490)<br>>1 (12190)<br>>2 (2014)<br>>3 (4) | 7.7 | 2.6 | 94 | 95 | 0.01 | 47 | 25 |

The methanogenic activity remained consistent during stabilization phase with a slight increase in the COD consumed (Table 3). To check higher methanogenic activity, we applied higher loading rate in last phase of incubation and result showed that more methanogenic activity as indicted by more gas production and a consistent COD reduction of around 90% was achieved.

Figure 5:
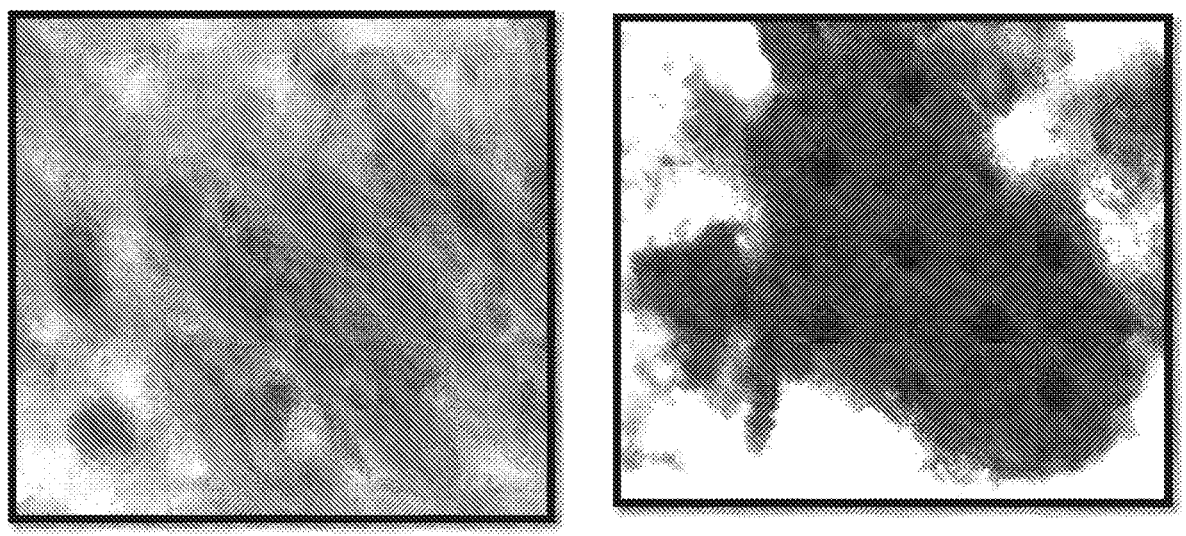
FIG. 5 illustrates Granule Picture as taken with Phase Contart Microscope (40×)

One of the embodiment of the invention includes use of granules filamentous bacteria, due to their particular morphology and surface properties, might establish bridges between several microflocs forming larger granules (>200 mm) Further development of acidogenic and syntrophic bacteria also favors the growth of the granules (As in Picture 1).

pH profile indicated that the reactor pH has been stabilized between 6.8 to 7.4. prior arts suggest that to avoid any inhibition of the methanogenic species that is needed for granulation, alkalinity has to be added. Further, it was established that the pH can be manipulated to the desired extent with the addition of $CaCO_3/CaCl_2$ directly to the reactor volumes so that the pH should remain above 6.5 at all times for optimum methanogenic activity and enhanced granulation. This allows VFA formation to increase without having as large an effect on pH as would be the case without the buffering. Surprisingly, in our experimentation we found that at many instances the inlet pH was significantly low but the outlet pH was quite stabilized without addition of any alkalinity and thus we have come to the conclusion that the synergic action the bacterial flora in our developed granules is able to balance the pH inside the reactor as shown Graph 3 of FIG. 5.

The elevated pH levels allows for the methanogenic conversion of VFA's to biogas and thus resulting in a far higher methanogenic activity, which in turn aids in the granulation process and breaks down the VFA's.

During the stabilization phase, the microbes (acidogens) convert most of the COD to ECP to buffer the pH and to protect them from their environment. After the pH has stabilized, COD is used for growth, and hence in the last section of the run, the granulation rate also increases dramatically.

Example 4: Study of Economics of Different Media and Effluents

Another important goal of this study is cost effective production of anaerobic granules. Prior art suggest that most researchers studied sludge granulation using synthetic wastewater. Therefore, in this work, effort was made to develop Granules using different types of wastewaters rich in carbohydrate. Keeping economics of granule production in view, pure carbohydrate medie has been replaced with actual industrial waste water (effluent). For this, industrial waste water of similar composition which has been applied to the biomass (Seed) for enhance granulation process in UASB. The feeding in UASB is continuously done with this various effluent obtained from Food Processing Units (FPU) rich in carbohydrate.

Granule counting done using plate-count method indicated that the granules formed by different FPU are almost similar in count. Also, microscopical observation revealed that their and size were also similar. All these waste water (effluent) yield almost similar type of granules as compared with pure synthetic media. Interestingly, the granule count was observed to be more in case of FPU effluents with high degree of satiability. Thus, these effluents can be used for cost effective production of anaerobic granules.

TABLE 3

Effect of media/Feed on granule size

| Media/Feed used | Granule Count/ml | Granule size > 1 mm | Granule size > 2 mm | MLSS (mg/l) | MLVSS (mg/l) | SVI ml/gm |
|---|---|---|---|---|---|---|
| Pure carbohydrate | 18900 | 12420 | 3780 | 56570 | 33090 | 10.16 |
| FPU | 29106 | 11880 | 3726 | 58248 | 29520 | 7.67 |
| FPU(M) | 25970 | 13500 | 4320 | 59250 | 41178 | 6.37 |
| FPU (B) | 24300 | 10800 | 3240 | 56660 | 34280 | 6.49 |
| Potato | 24570 | 9720 | 4590 | 52185 | 37051 | 6.93 |

Granule formation experiments using different media indicated that such carbohydrate rich waste water/effluent can also be used and that would give a huge saving of ~80-85% in production cost. Moreover, the waste water is also treated to meet land irrigation standards along with energy recovery making process 3 times efficient.

Example 5: Efficiency Study Using Different Media and Effluents

Phenomenon of granulation was first done using synthetic media containing pure carbohydrate in Lab scale UASB reactor. The same sludge granulation phenomenon has been then observed at similar loading rates using various food processing industry effluents and COD/BOD removal efficiencies over 90% has been observed along with higher biogas yields and very low VFA/ALK ratio.

TABLE 4

Efficiency of process during granule formation using different Media/Effluents

| Sr. No | Feed Type | Loading g COD/L/day | Gas produced L/day | COD REDUCTION % | BOD REDUCTION % | VFA/ALK ratio | TSS (mg/L) | VSS (mg/L) |
|---|---|---|---|---|---|---|---|---|
| 1 | Pure carbohydrate | 7.5 | 1.6 | 70 | 82 | 0.25 | 95 | 86 |
| 2 | FPU | 6.0 | 2.5 | 87 | 77 | 0.21 | 184 | 142 |
| 3 | FPU (B) | 7.0 | 1.5 | 94 | 90 | 0.005 | 35 | 16 |
| 4 | FPU(M) | 11 | 4.1 | 95 | 98 | 0.004 | 82 | 27 |
| 5 | Potato | 8.0 | 3.2 | 91 | 93 | 0.006 | 38 | 29 |

It is therefore concluded that the granular biomass produced in the present invention is very suitable for use in startup and reseeding of granular biomass in high rate anaerobic wastewater treatment reactors.

Example 6: Metagenomics Studies of Granules Prepared

Determination of the microbial diversity of the developed granulated sludge has been done using 16S rRNA metagenomics. Microbial DNA extraction was done from 1 ml of the granulated sludge sample using QIMP Stool mini kit. Extracted DNA was quantified using a Qubit fluorometric assay. To identify both Archaean and Bacterial population from the extracted DNA, specifically modified primers were used to amplify the 16S rRNA V3-V4 hypervariable region, followed by library generation to incorporate specific barcodes. The library was purified using AMPure XP beads. Accurate quantification of the purified library prior to pooling and loading onto the cartridge was performed using an in-house developed qPCR assay. The library was sequenced on an Illumina MiSeq next generation sequencer in a shared run using the Illumina V3 2*250 paired-end sequencing by synthesis chemistry. Resulting .fastq raw read files were analyzed using the 16S Metagenomics pipeline in the Illumina BaseSpace cloud analytical platform.

Further steps were essentially focused to obtain Operational Taxonomic Unit (OTU) and corresponding abundance, which involved o Aligning the quality improved sequence reads to the reference database and functional characterization of these samples, which largely included orthology based pathway analysis of the identified taxa which, in turn demonstrate the role of the identified taxa in the various biological pathways. Approximately 25% of detected organisms were Archaea and approximately 71% were Bacteria covering all types of microorganism (Picture 2) required for synergistic action to treat all types of organic waste/waste water.

According to prior art there is no known pathogenic methanogens or none of the other Archaea are pathogens either, but this is surprising to find that according to Metagenomics study the consortia of granulated sludge developed didn't contain any known human pathogen.

Methanogens also form close syntrophic associations with heterotrophic Bacteria that generate hydrogen (i.e. use protons as the terminal electron acceptor). Hydrogen-generating heterotrophism is only energetically favourable where the ambient concentration of hydrogen is extremely low.

Methanogens associate with other bacteria in this developed consortia, utilizes the hydrogen they generate for methanogenesis, and keep the hydrogen concentration low enough for the heterotrophs to make a living. Neither of these organisms could persist in the environment alone, but together they are successful. Hence Biogas is produced in the digester as a result of the activity of a consortium of anaerobic bacteria which decompose organic matter.

Example 7: Storage Study of Granules Developed

One of the key study which has been done is the study of Granules activity after its storage for different time period. Prior art suggest that methanogens show lower or no deterioration when stored at lower temp. It was surprisingly found that the Granules activity actually got enhanced after storage period of 3-6 months at ambient temperature (25-35 C). Although there has been some decrease in MLSS after the storage, but the granules showed higher degree of BOD & COD reduction and almost same amount of Biogas as compared to freshly developed granules (Table 5). We attribute this to growth of more methanogenic bacteria in the developed consortia while the decrease in overall MLSS is due to depletion in count of non-methanogenic bacteria. Thus, once again it is concluded that the granules formed is a robust consortia of all necessary bacteria required for synergistic action responsible for converting organic waste/waste water into its useful components and can used effectively over its storage period of 6 months.

| Sr. No. | Time period for storage (months) | MLSS/MLVSS (%) | SVI mg/ml | Loading g COD/L/day | Gas produced L/day | % COD REDUCTION | % BOD REDUCTION | VFA/ALK ratio | TSS (mg/L) | VSS (mg/L) |
|---|---|---|---|---|---|---|---|---|---|---|
| 1 | REVY-S (0 month) | 100% | 7.67 | 8.3 | 1.7 | 90 | 72 | 0.007 | 28 | 14 |
| 2 | 0-1 month old | 90% | 4.4 | 8.4 | 1.65 | 91 | 92 | 0.006 | 24 | 14.5 |
| 3 | 0-3 months old | 78% | 8.5 | 8.2 | 1.64 | 96 | 97 | 0.006 | 18 | 12 |
| 4 | 0-6 months old | 70% | 6.3 | 8.0 | 1.60 | 94 | 93 | 0.005 | 17 | 13 |

While the exemplary embodiments have been shown and described, it will be understood by those skilled in the art that various changes in form and details may be made thereto without departing from the spirit and scope of the present disclosure as defined by the appended claim.

I claim:

1. A process for preparation of anaerobic granules for waste water treatment comprising:
   a) introducing various feed media into different reactors containing an active biomass sludge with VSS content of 15000 mg/l and specific methanogen activity of 0.28 l/gm VSS and having bacterial aggregates of size below 1 mm;
   b) Use of simple sugars in the feed media and a source of nitrogen, phosphate and trace elements;
   c) providing mixing action to seed sludge with the media at a pre-determined temperature of 40° C. and 80 r-min-1;
   d) allowing formed micro anaerobic granules/seed sludge to settle for 9-24 day incubation;
   e) transferring of seed sludge as produced in step d) into an anaerobic reactor of cylindrical configuration and that operates in an anaerobic state;
   f) pure media or carbohydrate rich industrial effluent is introduced from the bottom portion of the anaerobic reactor; flows upwards through a seed sludge bed and is discharged through the upper portion of the anaerobic reactor;
   g) at least a part of discharged effluent from step f) is re-circulated at a predetermined temperature of 22-40° C. and an organic loading rate of 2.5-16.2 kg COD/$m^3 \cdot d$ and pH between 4.0 and 9.0; alkalinity of the reactor in a range of 750-1500 mg/l;
   h) Organic matter present in the pure media or waste water is removed by means of anaerobic treatment and granules are produced and simultaneously biogas, including methane, is also produced;
   i) repeating steps (f), (g), and (h), for 90-120 days until the seed sludge develops into Anaerobic Granules greater than or equal to 1 mm in size, having predetermined physical properties, is achieved.

2. A process for preparation of anaerobic granules for waste water treatment according to claim 1, wherein the trace elements used are specific multivalent cations B, Fe, Mn, Mg, Zn, Co, Ni, Al, Na, K Ca, Cu, Mo, Se, W and Vitamins folic acid, biotin, nicotinic acid and Vitamin B1, B2, B6, B12.

3. A process for preparation of anaerobic granules for waste water treatment according to claim 1, wherein the trace elements are vitamins and minerals.

4. A process for preparation of anaerobic granules for waste water treatment according to claim 1, wherein bacterial communities are 18-25% of archeal bacterial population, 45-48% of mixed function, 32-35% hydrogenotrophic and the rest are acetogenic.

5. A process for preparation of anaerobic granules for waste water treatment according to claim 1, wherein a yield is 80-98% of the biomass in the anaerobic reactor.

6. A process for preparation of anaerobic granules for waste water treatment according to claim 1, wherein the size of granule is 1-3 mm size.

7. A process for preparation of anaerobic granules for waste water treatment according to claim 1, wherein granulation of microorganisms is 99% of the biomass without any support material or polymer or no additional support material or polymer is used for agglutination of bacterial anaerobes.

8. A process for preparation of anaerobic granules for waste water treatement according to claim 1, wherein water treated with said granules is rich in nitrogen: TKN 7-9 mg/l, phosphorus: 10-50 mg/l, potassium: 3-9 mg/l and calcium: 150-350 mg/l and hence can be directly used as liquid fertilizer for irrigation of farm land.

9. A process for preparation of anaerobic granules for waste water treatment according to claim 1, wherein the anaerobic consortia are microorganisms selected from the group consisting of a microorganism strain S3/H4 MCC Accession No. 0116, so as to thereby degrade the matter in the sludge.

10. A method to effectively and economically treat waste water containing organic matter, using anaerobic granules produced as per the process in claim 1, thereby achieving COD & BOD reduction in a range 90-98%.

* * * * *